(12) United States Patent
Brue

(10) Patent No.: US 7,158,011 B2
(45) Date of Patent: Jan. 2, 2007

(54) MEDICATION COMPLIANCE DEVICE

(76) Inventor: Vesta L. Brue, 2635 Puesta Del Sol, Santa Barbara, CA (US) 93105

( * ) Notice: Subject to any disclaimer, the term of this patent is extended or adjusted under 35 U.S.C. 154(b) by 0 days.

(21) Appl. No.: 10/545,382

(22) PCT Filed: Feb. 16, 2004

(86) PCT No.: PCT/US2004/004358

§ 371 (c)(1),
(2), (4) Date: Jan. 23, 2006

(87) PCT Pub. No.: WO2004/073498

PCT Pub. Date: Sep. 2, 2004

(65) Prior Publication Data

US 2006/0139150 A1    Jun. 29, 2006

Related U.S. Application Data

(60) Provisional application No. 60/447,470, filed on Feb. 14, 2003.

(51) Int. Cl.
*G08B 1/00* (2006.01)

(52) U.S. Cl. .............. 340/309.16; 340/573.1; 340/531; 368/10; 368/244; 600/300

(58) Field of Classification Search ........ None
See application file for complete search history.

(56) References Cited

U.S. PATENT DOCUMENTS

| | | | |
|---|---|---|---|
| 4,572,403 A * | 2/1986 | Benaroya ................. 221/3 |
| 4,617,557 A | 10/1986 | Gordon | |
| 4,695,954 A | 9/1987 | Rose et al. | |
| 4,768,176 A | 8/1988 | Kehr et al. | |
| 4,768,177 A | 8/1988 | Kehr et al. | |
| 4,911,327 A * | 3/1990 | Shepherd et al. ........... 221/3 |
| 5,170,380 A * | 12/1992 | Howard et al. ........... 368/10 |
| 5,200,891 A | 4/1993 | Kehr et al. | |
| 5,313,439 A | 5/1994 | Albeck | |
| 5,408,443 A | 4/1995 | Weinberger | |
| 5,642,731 A | 7/1997 | Kehr | |
| 5,751,661 A | 5/1998 | Walters | |
| 5,752,235 A | 5/1998 | Kehr et al. | |

(Continued)

FOREIGN PATENT DOCUMENTS

CA    2212086 A1    1/1998

(Continued)

*Primary Examiner*—Benjamin C. Lee
(74) *Attorney, Agent, or Firm*—Hemingway & Hansen, LLP; Eugenia S. Hansen

(57) ABSTRACT

A portable medication compliance device (10) having a body (12) and compartments (22) formed in the body. A microprocessor (120) is disposed in the body (12) and is coupled to each of the compartments (22). The microprocessor (120) is programmable to determine relative time intervals for dispensing medication from each of the compartments, to notify the user when a dose of medication is to be taken from each of the compartments, and to record the opening of each of the compartments in a memory. Programming buttons (24) are positioned proximate the body and are coupled to the microprocessor (120). The programming buttons (24) enable a user to program the microprocessor. The device may also be programmed via a remote computer through communication means (47A). A display means (16) such as a Liquid Crystal Display (LCD) is positioned on the body and is coupled to the microprocessor (120). The LCD (16) displays data including the relative time intervals for dispensing medication determined by the microprocessor (120).

21 Claims, 6 Drawing Sheets

U.S. PATENT DOCUMENTS

| | | | |
|---|---|---|---|
| 5,755,218 A * | 5/1998 | Johansson et al. ..... 128/200.14 |
| 5,827,180 A | 10/1998 | Goodman |
| 5,850,937 A | 12/1998 | Rauche |
| 5,954,641 A | 9/1999 | Kehr et al. |
| D420,446 S | 2/2000 | Kehr et al. |
| 6,085,752 A | 7/2000 | Kehr et al. |
| 6,102,855 A | 8/2000 | Kehr et al. |
| 6,198,383 B1 | 3/2001 | Sekura et al. |
| 6,259,654 B1 | 7/2001 | de la Huerga |
| 6,424,599 B1 * | 7/2002 | Ditzig .......................... 368/10 |
| 6,439,422 B1 | 8/2002 | Papp et al. |
| 6,462,508 B1 | 10/2002 | Wang et al. |
| 6,524,240 B1 | 2/2003 | Thede |
| 6,529,446 B1 | 3/2003 | de la Huerga |
| 6,594,549 B1 | 7/2003 | Siegel |
| 6,601,729 B1 | 8/2003 | Papp |

FOREIGN PATENT DOCUMENTS

| | | |
|---|---|---|
| CA | 2251234 A1 | 12/1998 |
| GB | 2344194 A | 5/2000 |
| WO | WO 02/17850 A1 | 3/2002 |

* cited by examiner

MEDICATION COMPLIANCE DEVICE

CROSS REFERENCE TO RELATED APPLICATION

This application is a Rule 371 of PCT/US04/04358 filed Feb. 16, 2004 which claims the benefit of U.S. provisional application No. 60/447,470 filed Feb. 14, 2003.

TECHNICAL FIELD OF INVENTION

This invention relates to multi-compartment containers for pharmaceutical dosage forms comprising electronic means for signaling a user.

BACKGROUND OF THE INVENTION

Effective treatment of many common illnesses requires the administration of medications in a planned and controlled manner. Typically, a physician prescribes a course of treatment for a patient, and the patient is responsible for taking a prescribed medication according to the instructions of the physician. However, many studies have indicated that patients fail to comply with the physician's directives.

For example, a physician may prescribe multiple medications aimed at treating different aspects of an illness. As the number of medications prescribed increases, the responsibility on the part of the patient increases because of different dosages, intervals between dosages, and the like. Noncompliance is especially problematic when the illness being treated is chronic and extended therapeutic regimens are prescribed. However, research has determined that neither the severity of the illness being treated nor the potentially life-threatening consequences related to the patient's failure to follow the course of treatment prescribed by the treating physician significantly improve compliance.

Another problem that has been experienced by prescription drug users is the interaction between medications and/or special requirements that must be met when taking medications. For example, a physician may indicate that the prescribed medications must be taken in a certain order in order to maximize their efficiency with respect to treating specific diseases or disorders. In other cases, a physician may recommend that selected medications be taken with food or water. Other medications may be prescribed to be taken in the absence of alcohol or other intoxicants or medications. All of the directions and warnings must be observed by the patient so that the course of treatment will be safe and effective.

However, research has determined that prescription drug users often fail to comply with the instructions provided by the physician and/or the pharmacist. Many patients either forget to take a specific medication at all or otherwise fail to observe the warnings described above.

Research indicates that several factors appear to affect a patient's compliance with a prescribed course of treatment. These factors include (1) the accessibility of the medication at the prescribed time, (2) the forgetfulness of the patient, (3) the accountability of the patient to a person who is aware of the treatment prescribed and who may monitor the compliance of the patient, (4) the complexity and frequency of medication dosages, (5) prolonged use of the prescribed medication, and (6) the diminution of symptoms produced by the effectiveness of the medication, among other factors.

Patient's noncompliance with a prescribed regimen can lead to several problems. First, the desired effect of treatment may not be obtained. Second, when missing a dose, a patient may attempt to rectify the situation by taking an additional dose. However, a dose taken at the incorrect time and interval could have severe consequences for some drugs. In addition, irregular drug administration could lead to drug resistance. For instance, resistance to antibiotics is a severe problem in treating bacterial infection. Resistance to antiviral drugs has been reported to cause problems in treating HIV-positive patients, due to the fast replication of HIV virus and its ability to become dormant in the human body. The triple cocktail AZT is designed to suppress the generation of multi-resistance if patients follow strictly the drug regimen. However, even in this life-threatening disease, non-compliance is prevalent, and some studies have shown compliance rates as low as 16% (Laws et al. 2000, Taking antiretroviral therapy for HIV infection: learning from patients' stories. J. Gen. Intern. Med. 15(12), 848–858).

Patients generally rely on their memory and/or on manually operated medication dispensers to manage their treatment and their compliance with the instructions provided by the physician. For example, patients may rely on daily dosage pillboxes or similar devices to remind them to take their medication on a daily basis. However, these devices do not generally include any means for determining proper dosage intervals, especially for medications that must be taken more than once a day. Moreover, the devices do not provide any means for alerting a patient to the proper time and/or day for taking the prescribed medication.

Several efforts have been made to produce a device or method to help improve patient compliance with treatment regimens. U.S. Pat. No. 6,529,446 issued on Mar. 4, 2003 and U.S. Pat. No. 6,259,654 issued on Jul. 10, 2001 both to C. de la Huerga disclose a medication organizer with multiple vials secured to a unitary lid. Prescription and medication information is stored in a memory chip attached to the vial, which can be detected by the sensors in the unitary lid. The microprocessor determines the time of medication and reminds the patient with audible and visual alerts and a display, and the compliance information can be stored and communicated remotely. The device requires preparation of separate vials with individual memory chips each time a drug is dispensed by a pharmacist.

Canadian Patent Application No. 2,251,234 published on Dec. 12, 1998 to J. M. Girgis discloses a portable medication reminder and compliance device. The disclosed device contains several medication compartments with a single LCD display providing medication information and messages, and alerting patients at medication times. The compliance data can be stored and communicated remotely. However, the medication compartments either contain no lid, or just a simple cover with no control mechanism. Furthermore, the alert signals must be manually silenced in order to be recorded as an event of compliance.

U.S. Pat. No. 5,850,937 issued on Dec. 22, 1998 to S. J. Rauche discloses a pill dispenser with means to alert users of the time of medication, and the medication compartments are organized by each day of week or each day of month. The device requires input of a personal identification number or PIN for each user at each medication time, and the access of pills requires matching of correct PIN at each of the medication time.

Canadian Patent Application No. 2,212,086 published on Jan. 31, 1998 to H. Ho and A. Chan discloses a medication storage device with the compartments organized in each day of month, and a separate reminder unit providing visual and vibration alerts.

A pill organizer as disclosed in UK Patent No. GB 2,344194 filed on Nov. 25, 1998 by K. Doughty discloses medication compartments organized by multiple periods in a day for 8 days. In one embodiment, the compartments are sealed by film and the puncture of film is recorded as an event of medication compliance.

U.S. Pat. No. 4,617,557 issued on Oct. 14, 1986 to R. E. Gordon discloses a device specially designed for use with a blister package, having alert mechanism. The display is significantly abbreviated due to a limited display area. It reminds the user of the medication time by displaying time to next dose. The blister package needs to be specially prepared for each medication, and a patient may require multiple sets for multiple medications.

U.S. Pat. No. 6,198,383 issued on Mar. 6, 2001 to R. D. Sekura and C. M. Sekura discloses a small medication compliance device for single or multiple medications. The device reminds a user of the time to take medication, and it contains an event switch activated by a user after taking medication. The device is small enough to be attached to medication compartments which are physically separate, and the device further includes a remote programming feature via a wireless link.

Despite previous efforts in the area of medical compliance devices, many of the devices heretofore reported are either cumbersome (e.g., the devices are not portable), expensive, lack desired functionality, or require complicated procedures for programming. Moreover, many prior devices and methods are complicated and difficult to use, especially for patients having diminished physical and mental abilities. Therefore, there is a need for a simple but effective device that will assist a patient in managing their intake of prescription or over-the-counter medications and compliance with prescribed regimens.

SUMMARY OF THE INVENTION

In one aspect, the invention comprises a portable medication compliance device, including a body; a plurality of compartments formed in said body, a memory disposed in said body adapted to contain one or more pharmaceutical dosage forms; a programmable microprocessor disposed in said body and operatively coupled to said memory and each of said compartments, and at least one display means in said body operatively coupled to said microprocessor, and adapted to display information as to when a dose of medication is to be taken from each of said compartments, to the user.

In one embodiment, the device may be programmed by the user, and a plurality of programming buttons are disposed proximate said body and operatively coupled to said microprocessor. In another embodiment, programming information may be downloaded to the microprocessor from a remote computer. Preferably, the portable compliance device further comprises output means for signaling, which serve to alert a user of the time to take a particular type of medication. In a preferred embodiment, the compliance device further comprises a communication port operative to enable the uploading of compliance from the device memory to a remote device or computer, or to enable downloading information from a remote device or computer to the microprocessor and memory coupled thereto. In a preferred embodiment, the display means comprises one or more LCD displays for displaying information. One preferred embodiment comprises a plurality of LCD displays to display information for individual medication compartments, each of said LCD display disposed proximate each of said medication compartments.

In another embodiment, the compliance device further comprises a charger connector configured to interface with a device connector of a battery charger. Preferably the battery charger contains a power supplying device for transforming inputted AC or DC power into a predetermined voltage to supply power to the portable device when the charger connector and the device connector are engaged. The device connector is preferably housed in a cradle adapted to receive the device for charging and configured to engage the charger connector on the device. In another embodiment, the compliance device further comprises audible, visual and/or vibration means to alert a user of the time to take a particular type of medication, said audible and visual means operatively coupled to and activated by said microprocessor when said relative time interval to take a dosage form expires. The cradle may also comprise a communications port adapted to receive a communications line such as a phone line or cable, and means for communicating with said device.

In another aspect, the invention is a portable medication compliance device containing a body adapted to be transported by a user; a plurality of compartments formed in said body, adapted to contain one or more pharmaceutical dosage forms. Each of said compartments having a lid operatively coupled thereto; a memory disposed in said body; at least one display means disposed on said body; and a microprocessor disposed in said body. The microprocessor is operatively coupled to said memory, each of said compartments and said LCD display. The microprocessor is programmable to determine time for dispensing medication from each of said compartments, to notify the user when a dose of medication is to be taken from each of said compartments. The microprocessor may also record the opening of each of said compartments in said memory. A plurality of programming buttons is preferably disposed proximate said body and operatively coupled to the microprocessor, the plurality of said programming buttons adapted to enable the user to program said microprocessor. One or more compartment buttons may be provided, each said compartment button disposed on one of said medication compartments, and operatively coupled to said microprocessor, said display means and said memory. The compartment buttons may be operatively responsive to different modes of manual operation. For example, pressing one of said compartment buttons may activate display functions; and pressing one of said compartment buttons twice may serve to open the compartment to allow access to medication; while pressing the compartment button and holding it down several seconds may activate the programming function.

In a preferred embodiment, the compliance device also comprises a microprocessor programmable to determine the relative time interval to take a pharmaceutical dosage form. The relative time interval may be determined based on the dose frequency selected by a user via programming buttons; or via programming from a remote computer. Opening of the medication compartment preferably resets the relative time interval. In another embodiment, the compliance device further comprising audible and visual means to alert a user of the time to take a particular type of medication. The said audible and visual means are operatively coupled to and activated by said microprocessor when said relative time interval to take a particular medication expires. In another embodiment, a prerecorded voice message announcements verbally repeat the warnings appropriate to the compartment and the number of pills to remove at time of lid openings.

BRIEF DESCRIPTION OF THE DRAWINGS

The present invention will be better understood with reference to the accompanying drawing in conjunction with the detailed description. The drawings in the detailed description are of preferred embodiments of the invention and, thus, are not to be considered limiting.

DETAILED DESCRIPTION OF THE INVENTION

A medication compliance device according to one or more aspects of the present invention comprises a portable, effective mechanism for assisting patients in complying with a course of treatment. The device may be used by a patient to comply with a medication schedule prescribed by a physician. However, the medication compliance device is not limited to use with prescription medications and may be used without a physician's directive. For example, the device may be available over-the-counter so that users may purchase the medication compliance device without a prescription from a physician and use the device with over-the-counter medications, presented in one or more pharmaceutical dosage forms, such as tablets, pills or capsules, for example.

The medication compliance device will be described below with respect to several characteristics including a physical description of embodiments of the medication compliance device; signaling and recording functions of the device; remote communication with the device; and remote access to user data uploaded from the device.

Physical Characteristics of the Medication Compliance Device

Figure 1:
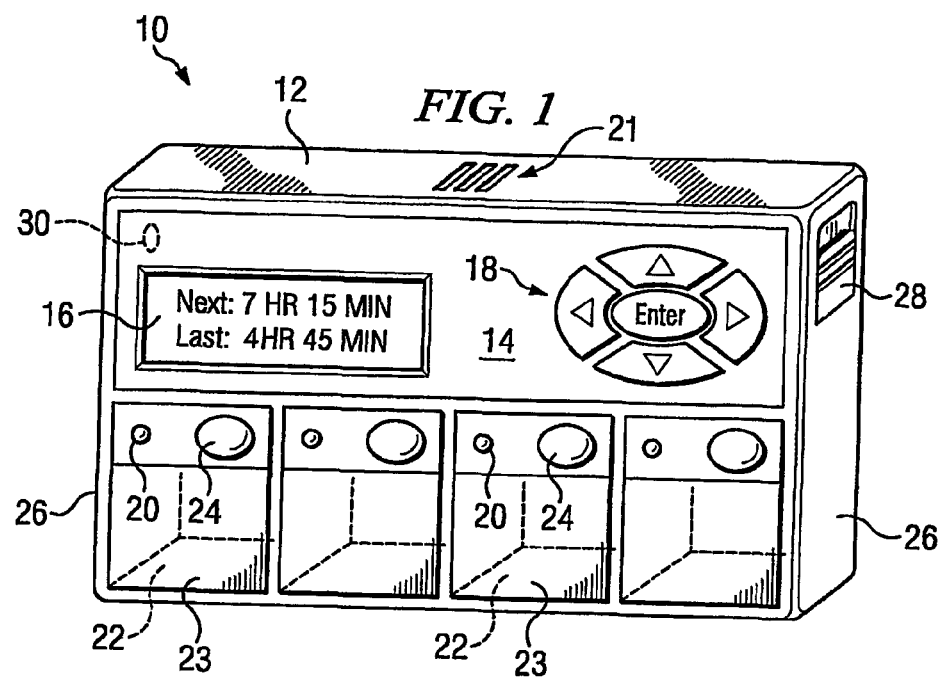
FIG. 1 depicts a perspective view of an embodiment of the medication compliance device.
Figure 5:
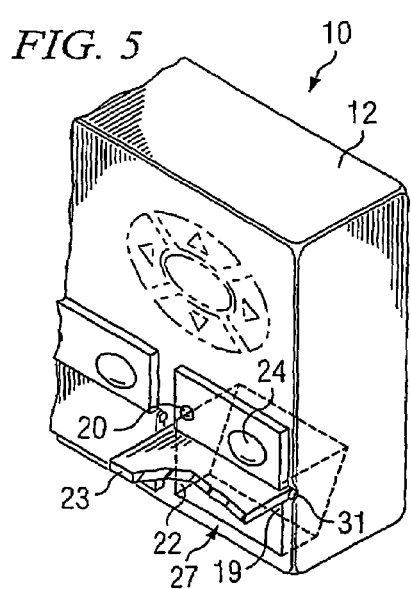
FIG. 5 depicts a partial section view of an embodiment shown in FIG. 1 with the compartment lid in the open position.

An embodiment of a medication compliance device 10 is shown in FIG. 1. The device 10 comprises a substantially rectangular body 12 that may be formed from plastic, metal, or other suitable materials. The device 10 has an upper surface 14 that includes a display means 16 for messages, at least one programming button 18, light emitting diodes (LED) 20, a plurality of medication compartments 22, and a plurality of medication compartment buttons 24. Lid 23 opens and closes as best seen in FIG. 5. Device 10 also includes sides 26 that include a battery compartment 28, a communication port 30, and output means 21 for a signaling device located inside device 10. Note that the locations of the various components of the device 10 may vary in other embodiments. For example, the battery compartment 28 may be disposed on a lower surface (not shown in FIG. 1) of the device 10. Accordingly, the specific arrangement of, for example, the battery compartment 28, output means device 21, and the communication port 30 are not critical. Therefore, the specific physical arrangement shown in FIG. 1 is not intended to limit the scope of the invention.

The body 12 of the medication compliance device 10 is designed so that the device 10 may be easily carried in, for example, a purse, a shirt pocket, and the like. Moreover, the device 10 is adapted to be easily grasped and handled so that the operational features of the device 10 including, for example, the medication compartment buttons 24, may be easily manipulated. In a preferred embodiment as shown in FIG. 1, the device 10 is approximately 12 cm long, approximately 6 cm wide, and approximately 1.5 cm deep. Note that the physical dimensions of the body 12 may be varied within the scope of the invention and that the measurements provided above are intended only to illustrate the compact nature of one of the embodiments of the medication compliance device 10.

In the embodiment shown in FIG. 1, the display means is a liquid crystal display (LCD) 16. The display means may be any suitable structure which may receive electronic information and display the information as characters and words. In a preferred embodiment, LCD 16 includes a two line display with for example, 14 to 16 characters per line. The LCD shown in FIG. 1 is approximately 6 cm wide and 2.5 cm high. Note, however, that the dimensions of the LCD 16 are not critical and are not intended to be limiting. Other embodiments may include an LCD with additional lines of text display or with more or fewer characters per line.

The LCD 16 uses standard alphanumeric characters in approximately a 12 point font. Larger font sizes may be used, however, to assist visually impaired users and the like, and smaller font sizes may be used to display more information on the LCD. As discussed below, the LCD 16 both displays information related to medication dosage and delivery and enables on-screen programming of the medication compliance device 10. The LCD 16 also displays reminders and warnings and may include a backlight so that the device 10 may be used in low-light conditions.

Note that other embodiments may include a separate LCD for each compartment so that specific information for each compartment may be displayed on individual LCDs. Alternatively, a single LCD may be used to simultaneously display information related to each of the compartments. The single LCD displays information appropriate to each compartment when the button of that compartment has been pressed or when the lid is opened. The LED for the compartment will be activated to illuminate when the lid is opened or the button pressed. Thus, if the information shown on the LCD will apply to the compartment with an illuminated LED. If the patient's prescribed regimen involves taking multiple medications at approximately the same time, the LCD displays information corresponding to each medication in order and also identifies the compartment containing the medication by a letter, word, or symbol such as, for example, A, B, C, or D, or #1, #2, #3 or #4. In an alternative embodiment, the device has a plurality of LCD displays, and each display provides information corresponding to a particular medication compartment or compartments.

Figure 2A:
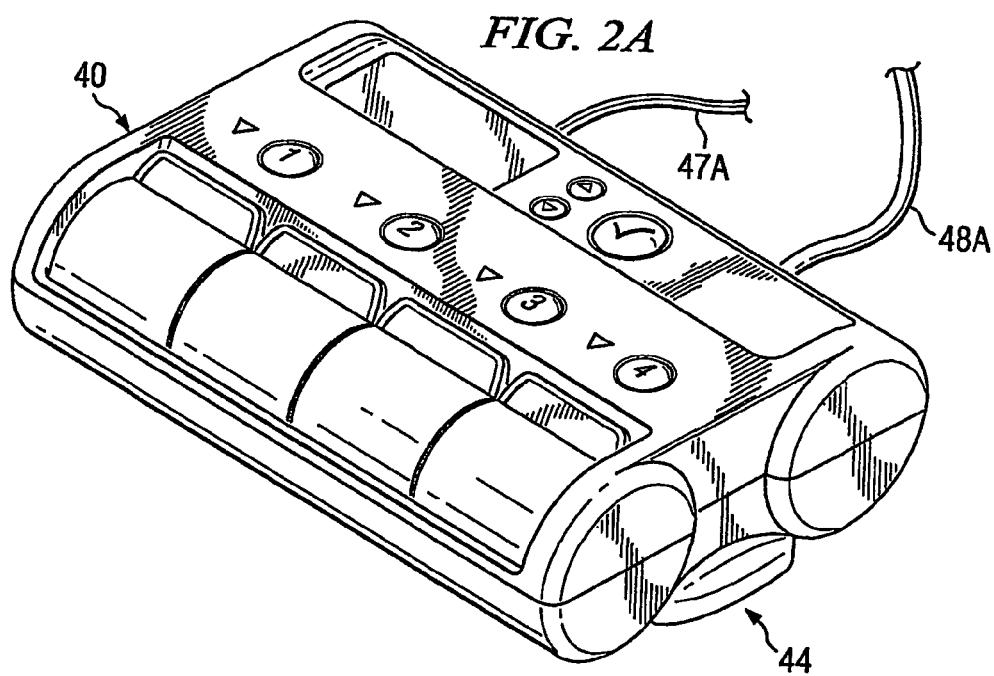
FIG. 2A depicts device 40 of FIG. 2 engaged with cradle 44 of FIG. 2 with power cord 48A and communications lines 47A attached for charging and/or communication with a remote computer.
Figure 2:
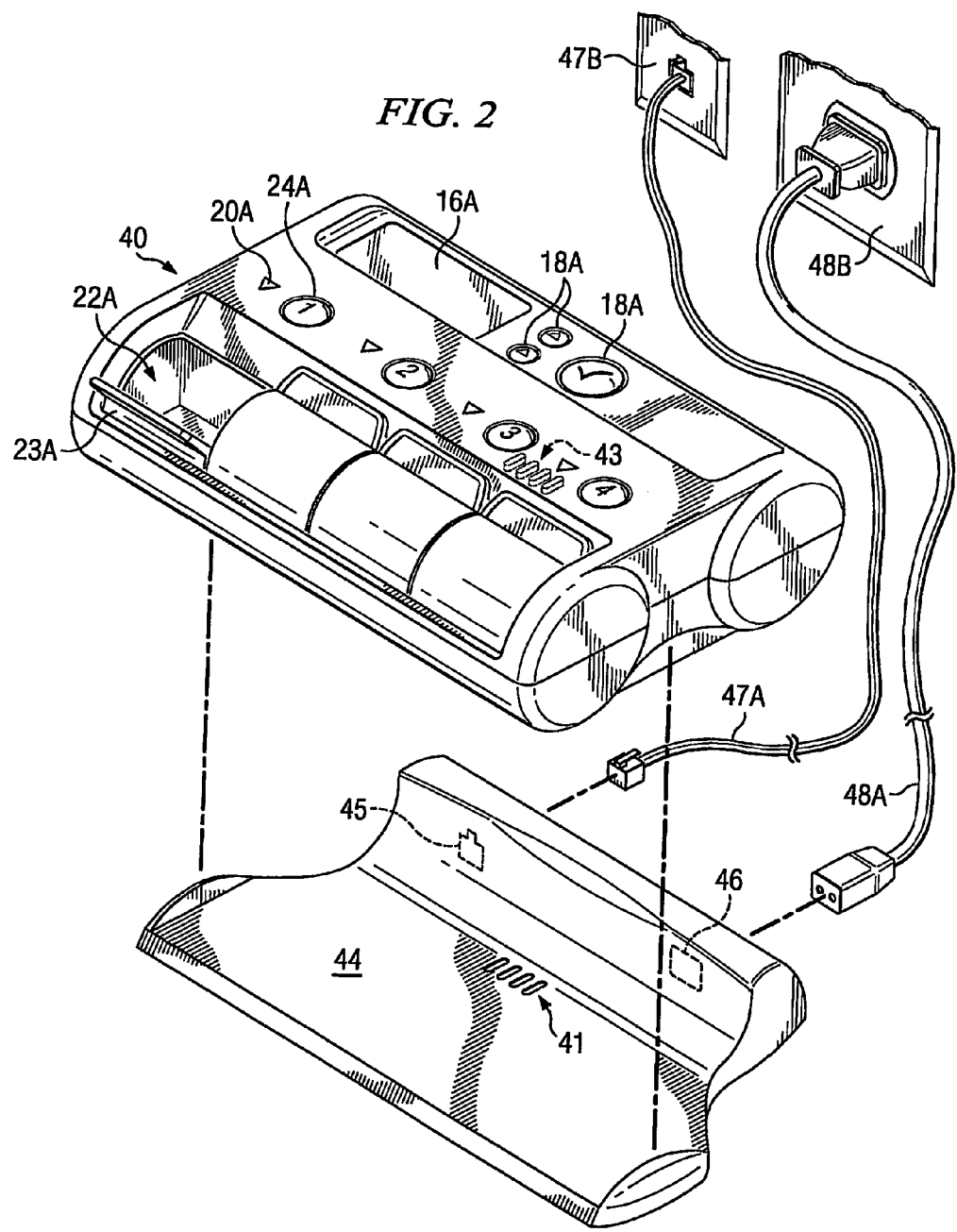
FIG. 2 depicts a perspective view of another embodiment of the medication compliance device and a cradle for receiving the device in engaging relationship for charging and/or remote communication means.

Another embodiment of the device consists of a portable device 40 and a cradle 44 as shown in FIG. 2. The components labeled 16A, 18A, 20A, 22A and 23A generally correspond to items 16, 18, 20, 22 and 23 in FIG. 1. The cradle 44 comprises a battery charger and a means for remote communication. Communication port 45 permits connection of a communication line 47A (such as a phone line or cable) which may be connected to standard phone jack or cable outlet 47B. The cradle 44 also contains a power connector 46 to be connected to a power cord 48A which may be conveniently connected to a standard AC wall outlet 48B, when a transformer providing step-down voltage is integrated in cradle 44. Alternatively, a plug-mounted transformer (not shown) which provides a step-down voltage may be used. Furthermore, the cradle 44 comprises a device connector 41 comprising a device power contact and a device communication contact. Device 40 also contains a corresponding charger connector 43 comprising a charger power contact and a charger communication contact. Through the engagement of 41 and 43, the rechargeable battery in the device is regularly recharged through the engaged power contact and any data collected in memory of device 40 can be communicated to a remote server via the engaged communication contacts which interface through communications port 45 and communication line 47A. FIG. 2A depicts device 40 placed in cradle 44 in engaged position with line 47A and power cord 48A connected to cradle 44. Alternatively, device connector 41 and charger connector 43 may include only a power contact, communications being instead received by the device through wireless communication means. In such case, cradle 44 may not include part 45 to receive a communication line, unless two modes of communication are desired.

Figure 7:
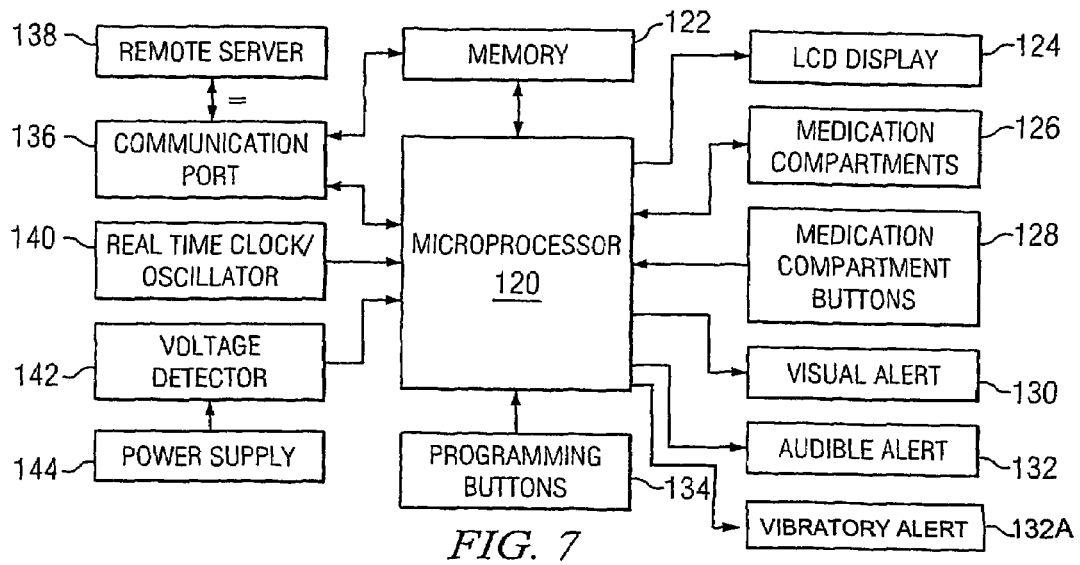
FIG. 7 depicts a block diagram representation of the electronic circuit of the medication compliance device.

Embodiments of the medical compliance device also comprise electronic circuitry associated with the various physical aspects of the device. FIG. 7 shows a block diagram of an electronic circuit illustrating the connection of different components of the device. The operation of the device is controlled by a microprocessor 120, which is operatively coupled to a memory 122. In one embodiment, the memory is EEPROM which is erasable, so that the device can be programmed more than once, and the compliance data stored in the memory can be erased to make room for new data. Communication port 136 (represented in FIG. 1 as 30 and in FIG. 2 as 45) can be connected to the microprocessor 120, memory 122 and a remote server 138 to allow uploading of data from the device or alternatively downloading programs and instructions from the remote server.

In FIG. 7, the microprocessor 120 is operatively coupled to various features including the LCD 124, the programming buttons 134, sensors within the lids of medication compartments 126, the medication compartment buttons 128, the visual alert LEDs 130, the audible and/or vibrating signaling device 132. Real time clock 140 interfaces with the microprocessor to provide data on the time and day. A type of power supply 144, such as a battery, powers the device, and the electronic circuit preferably contains a voltage detector 142 to sense levels of power remaining and to send alerting signals when the battery is low.

Connections between the microprocessor, the memory, and the other aspects of the medication compliance device are completed using methods that are well known in the art. For example, various embodiments of the invention comprise printed circuit boards and the like that operatively couple selected elements of the medication compliance device to the microprocessor, the memory, the battery, and to each other. Referring to FIG. 1, the signaling device 21 may be a speaker or any other similar device that provides an audible signal that may be heard by the user. Alternatively, a visual or vibrating signaling device may be employed.

The specific circuitry and connectivity of the various aspects of the invention may be made according to means and methods well known in the art. Accordingly, the specific circuitry and connectivity of the various elements are not intended to limit the scope of the invention. The following discussions related to the programming and operative nature of the medication compliance device will be provided with the understanding that the functionality can be achieved using methods and hardware that are known in the art.

Referring again to FIG. 1, medication compartments 22 are disposed on the upper surface 14 of the body 12. The embodiment shown in FIG. 1 has four compartments 22 arranged in a line, and each compartment 22 is sized to carry a suitable supply of medication. The number of medical compartments and their arrangement could vary in other embodiments. Note that the number of pills to be taken at each dosage interval and the physical size of each pill may limit the numbers of doses that may be stored in each compartment 22. However, in a preferred embodiment, each compartment 22 is sized to hold approximately a seven day supply of a selected medication. Another embodiment that comprises a smaller version of the medication compliance device may contain only a one day supply of a selected medication. Accordingly, the medication compartments may be selectively sized and the quantity of medication that they may contain is not intended to limit the scope of the invention.

Each compartment 22 is also preferably designed so that medication may be easily accessed and grasped. For example, in the embodiment shown in FIG. 1, the preferred dimensions of each compartment 22 are approximately 5.6 cm wide, approximately 2.5 cm high, and approximately 0.8 cm deep. A bottom surface 19 (as shown in FIG. 5) of the compartments 22 may be sloped or angled to facilitate easier access to the medication contained therein. In a preferred embodiment, the compartments are identified individually by a letter, word, color or symbol such as A, B, C or D or alternatively #1, #2, #3 or #4 scripted on one side of compartment wall or color lids. The word or number label may also appear on the compartment lid 23, or alternatively on the body proximate the compartment. The marking should be easy to view. The labeling of each compartment has two advantages, first, the medication information displayed on LCD could identify specific compartment to minimize potential confusion, especially when multiple medications are to be taken at the same time. Another advantage is to provide a simple route of programming multiple compartment at the same time (for details see below section on Programming the Medication Compliance Device).

Referring to FIG. 5, each compartment 22 also includes an associated lid 23 coupled thereto. Each lid 23 may be, for example, ratably coupled to a respective compartment 22 or to the body 12. Other embodiments may include lids 23 that are slidably coupled or removably coupled to the compartments 22 or to the body 12 using any suitable means known in the art. The embodiment shown in FIG. 5 includes hinges 31 that rotatably couple the lids 23 to the respective compartments 22. The hinges 31 enable the lids 23 to rotate with respect to the body 12 to enable easy access to the compartments 22. In one embodiment, the lids 23 are adapted to rotate approximately 180 degrees with respect to the body 12. In another embodiment, the lids 23 are adapted to rotate about the hinges 31 by approximately 90 degrees with respect to the body 12. Each compartment 22 and/or lid 23 is preferably operatively coupled to the microprocessor so that the time of opening and/or closing of the compartment may be recorded and stored in the memory. In the alternate embodiment as shown in FIG. 2, one compartment is shown with the lid in opened position, and the lid is shown rotatably coupled to the device 40.

Preferably, the lids of the compartments are approximately 2.5 cm long and approximately 2.5 cm wide. Referring to FIG. 5, opening 27 permits a finger to be inserted to access medication in the compartment 22. Each lid 23 may also include a label attached thereto to indicate, for example, the type of medication contained in the associated compartment 22. The label may be any type of label known in the art and may be replaceable so that it can be changed along with the medication contained in the selected compartment.

Each compartment 22 in FIG. 1 also includes at least one light-emitting diode (LED) 20 and a medication compartment button 24. The at least one LED 20 provides a visual reminder when a dosage in a selected compartment 22 is to be taken and when LCD information applies to the selected compartment. Other visual indicators known in the art may also be used. For example, as will be described in detail below, the LED 20 is operatively coupled to the microprocessor and may blink a selected number of times when a prescheduled dosage should be taken from the selected compartment 22. Moreover, the number of blinks in a selected period of time may indicate the number of pills to be taken from the selected compartment 22. Note that some embodiments may include multiple LEDs disposed proximate each compartment. For example, the number of LEDs may be selected to correspond to a number of pills and the like that are to be taken from the compartment in a selected dose. In other embodiments, multiple LEDs may be positioned proximate the compartment, and a selected number of the LEDs may be illuminated (as described in detail below) wherein the number of illuminated LEDs corresponds to the proper dosage.

Figure 3:
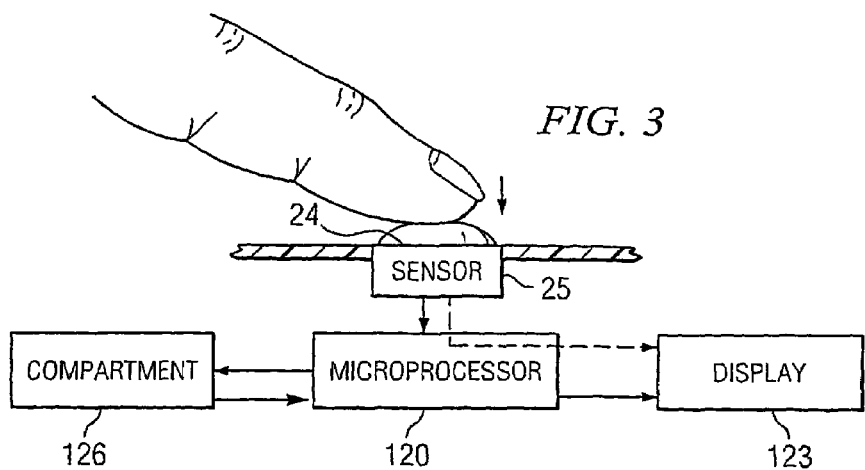
FIG. 3 depicts activating a compartment button with one slight pressure from a finger of a user, thereby causing the microprocessor to activate the display function.

Referring to FIG. 1 and FIG. 2, the medication compartment buttons 24 and 24A respectively, are disposed proximate the associated compartments 22. In one embodiment, shown in FIG. 3, when compartment button 24 is depressed once, the sensor 25 beneath the button causes microprocessor 120 to activate the display function 123. The LCD 16 (FIG. 1) or 16A (FIG. 2) may be used to display two lines of text including any of the following data, among other data: (1) the elapsed time since the last dose from that compartment 22 was taken; (2) the time remaining until the next scheduled dose; (3) the number of lid openings that have been recorded for that compartment in the current day, the last two intervals; (4) the number of pills to be taken in the next dose; (5) contra-indications; and (6) directions for taking the medication (e.g., take with food, water, etc.). Tapping compartment button 24 together with one of the programming buttons 18 (FIG. 1) or 18A (FIG. 2) may be used to activate the programming function (see description below).

Figure 4:
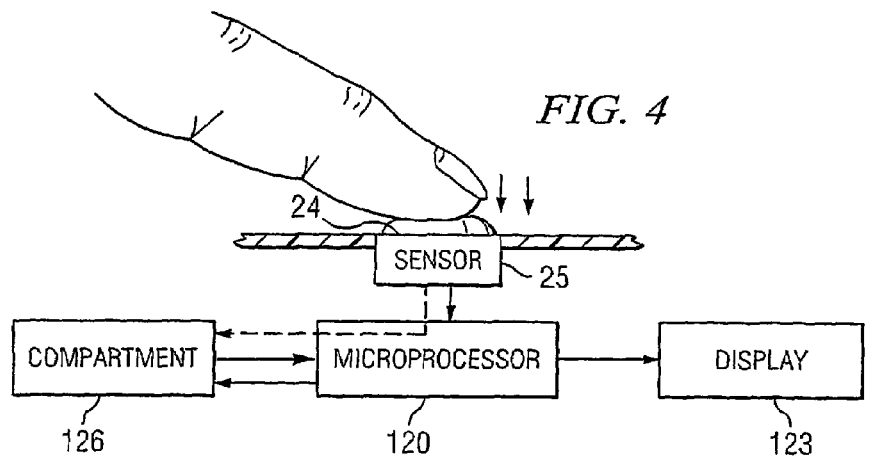
FIG. 4 depicts activating a compartment button by pressing two times in rapid succession thereby causing the microprocessor to activate the lid opening release function.

In another embodiment as shown in FIG. 4, when a compartment button 24 is depressed multiple times, in rapid succession such as preferably two times, the sensor 25 beneath the button sends signal to the microprocessor 120 to cause the compartment 126 to open so that the user can access the medication disposed in the selected compartment. The variation in number of presses required to either display data (e.g., text on the LCD 16) or to open the compartments (using the release buttons 24) helps prevent the compartments 22 from accidentally opening when the medication compliance device is disposed in a purse, pants pocket, shirt pocket, and the like. Opening of the compartment sends a signal back to the microprocessor. Moreover, causing multiple rapid succession presses to activate the compartment rather than a single press also provides a child-safety feature in that it is more difficult for small children to open an unattended device. In another embodiment, the lid 23 (FIG. 1 or 23A (FIG. 2) can be opened mechanically to allow retrieval of medications. The compartment button may also be operatively linked to the sensor so that when the button is depressed firmly for several seconds (e.g. 3 seconds), the microprocessor sends a signal to activate the programming mode.

Figure 6:
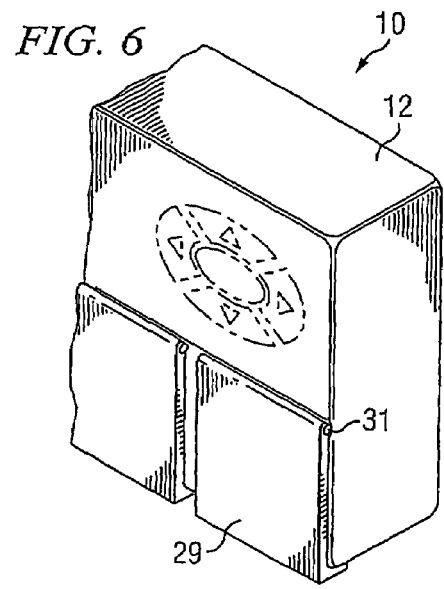
FIG. 6 depicts a partial perspective view of an embodiment of the present invention showing a keyguard feature.

In some embodiments, the medication compliance device 10 may include a keyguard. For example, the embodiment shown in FIG. 6 includes a keyguard 29 that substantially covers all of the compartment buttons (24 in FIG. 1) on the device 10. The keyguard 29 may be coupled to the body 12 or the compartments (22 in FIG. 1) using the hinges 31 that couple the lids (23 in FIG. 1) to the body 12 or any other attachment means known in the art. The keyguard 29 may prevent accidental opening of the compartments (22 in FIG. 1) and may help prevent children from accessing medication in the compartments (22 in FIG. 1). In other embodiments, an electronic keyguard may be used so that a user must enter a selected, user-defined "code" to activate the buttons (24 in FIG. 1). In these embodiments, the correct code must be entered using, for example, programming buttons 18 in FIG. 1 such as those described below to "unlock" the release buttons, the programming buttons themselves, and the like. This coded access requirement embodiment may be used for narcotic or psychopharmacologies in which the user seeks to prevent tampering or theft. In another embodiment, the user-defined "code" (equivalent to a PIN) is used to identify compliance data, and remotely communicated to a pharmacist or a doctor for monitoring or data storage purpose.

The upper surface 14 also includes programming buttons 18. As will be described in detail below, the programming buttons 18 are used to program the medication compliance device 10. While the buttons will be generally described as "programming buttons," the programming buttons 18 may include, as illustrated in FIG. 1, an "Enter" button, up and down arrow buttons, and/or left and right arrow buttons. Another embodiment as shown in FIG. 2 contains only 3 programming buttons including 18A the "Enter" button, and the up and down arrow buttons. Alternatively, the device 10 may include a keyboard, joystick, touch pad, or similar device that may be used to program and/or operate the device. Accordingly, the generic description of the buttons as "programming buttons" is not intended to limit the scope of the invention. Note that, as described above, the programming buttons 18 and 18A are operatively coupled to the microprocessor 120.

Similarly, the communication port 30 in FIG. 1 enables the device 10 to be connected to a computer or communications time line so that the device 10 may remotely communicate with, for example, another computer or programming device. It will also be appreciated for those skilled in the art that the communication port 30 could also be provided by an infra-red link for wireless connection. A traditional communications port such as illustrated in FIG. 2 at 45 that may be engaged with 47A phone line or cable can be provided directly to device 10 or 40 instead of using wireless port 30 as shown on FIG. 1 or connecting to cradle 44 as shown in FIG. 2. In such case a communications port may be provided on side 26 or on the back of the device with similar structure illustrated with respect to communications port 45 of cradle 44.

The medication compliance device 10 (FIG. 1) or 40 (FIG. 2) may use disposable batteries, rechargeable batteries, or other power sources that may require the use of various types of power adapters. The embodiment shown in FIG. 1 is adapted to operate using one size "AA" battery that is commonly available. The embodiment in FIG. 2 is shown with a rechargeable battery in the portable device 40. When the device 40 is connected to the cradle 44, the battery is recharged regularly through the device contact 41 on the cradle 44 and the corresponding cradle contact 43 of portable device 40. A power cord 48A may be connected to the power connector 46 of the cradle 44 and 48A may be plugged into a standard AC wall outlet 48B as illustrated or other suitable power source. Some embodiments of the medication compliance device may be equipped with long-lasting lithium-ion batteries in order to extend the time between battery replacement. Moreover, other embodiments may also include an AC adapter port (not shown) that enables the device 10 to operate using power from a standard household supply, a 12V power outlet in an automobile, and the like. The device also preferably includes a "sleep" mode that helps conserve battery power. The sleep mode may be activated if the device is idle for a selected period of time (e.g., between dosages and the like). While in the sleep mode, the device continues to track the dosage schedule, but, for example, the display 16 (FIG. 1) or 16A (FIG. 2) may be blank during this time.

In a preferred embodiment, the device includes a low battery detection means which is operatively coupled to the battery and the microprocessor. When the batteries in the device reach a first predetermined power level, the LCD 16 will display a "low battery" message. The predetermined power level may be selected to enable the device 10 to continue to operate at the low battery level for several days so that the user has an extended warning period and can change the batteries before the device 10 completely powers off. If the low battery warnings are ignored, the LCD 16 will cease to operate when the batteries reach a second predetermined low battery power level. The LEDs 20 and the output means for signaling 21 may then provide both visual and audible alerts for a selected time period, after which the alarm functions will also cease to operate. The medication compliance device 10 will continue to record the opening of the compartments 22 until all battery power is lost. When the batteries are completely drained, the compartments 22 can no longer be opened until the batteries are replaced, recharged, etc. In a preferred embodiment, the memory is static so that information written to it during programming remains stable during battery replacement. An example of such memory is EPROM memory. However, in other embodiments, the compartments 22 may include a manual override key and the like so that the user can access the medication inside the compartment in an emergency situation (e.g., if the batteries are dislodged, the device malfunctions, replacement batteries are unavailable, and the like). In a preferred embodiment, replacing the battery does not affect the relative time interval of the device which is timed internally by an oscillator.

Programming the Medication Compliance Device

Programming the medication compliance device as described herein generally relates to programming the microprocessor 120. The medication compliance device 10 may be programmed to help a user maintain a course of treatment. In a preferred embodiment, programming is performed by the user using the programming buttons 18 and the LCD 16 in FIGS. 1 and 18A and 16A in FIG. 2. However, programming may also be performed by downloading programming information via the Internet, from a remote or local computer, server, a handheld computing device, or other device coupled to the communication port 30, or by other suitable means. For example, a user may connect the medication compliance device 10 (FIG. 1) or 40 (FIG. 2) to a remote device via the communication port 30 (FIG. 1) or 45 (FIG. 2). The remote device may be a LAN, an Internet connection, or a remote computer or server. The user may download programming instructions provided by a treating physician or other party directly to the memory operatively coupled to the microprocessor. The programming instructions may then be implemented by the microprocessor and the medication compliance device to assist the user in maintaining a selected medication dosage regime.

Therefore, the medication compliance device may be programmed in several different manners. While the following description generally relates to programming the device such as illustrated in FIG. 1 (10) or FIG. 2 (40) using the programming buttons 18 or 18A disposed on the device 10 or 40, the description is intended to illustrate the programming features of the device and is not intended to limit the device to manual programming capabilities.

A preferred embodiment of the medication compliance device operates on a "relative time" basis. For example, the device operates to manage a dosage schedule according to fixed intervals between doses without reference to a "traditional" 24-hour time system. Instead of displaying the next dose as due at "8:00 PM," the device manages doses as due in, for example, "7 hours, 34 minutes." The use of fixed, relative time intervals that do not rely on a 24-hour time system eliminate the effect of time zones, daylight savings time, and the like so that a simple, effective dose schedule is maintained.

Figure 8:
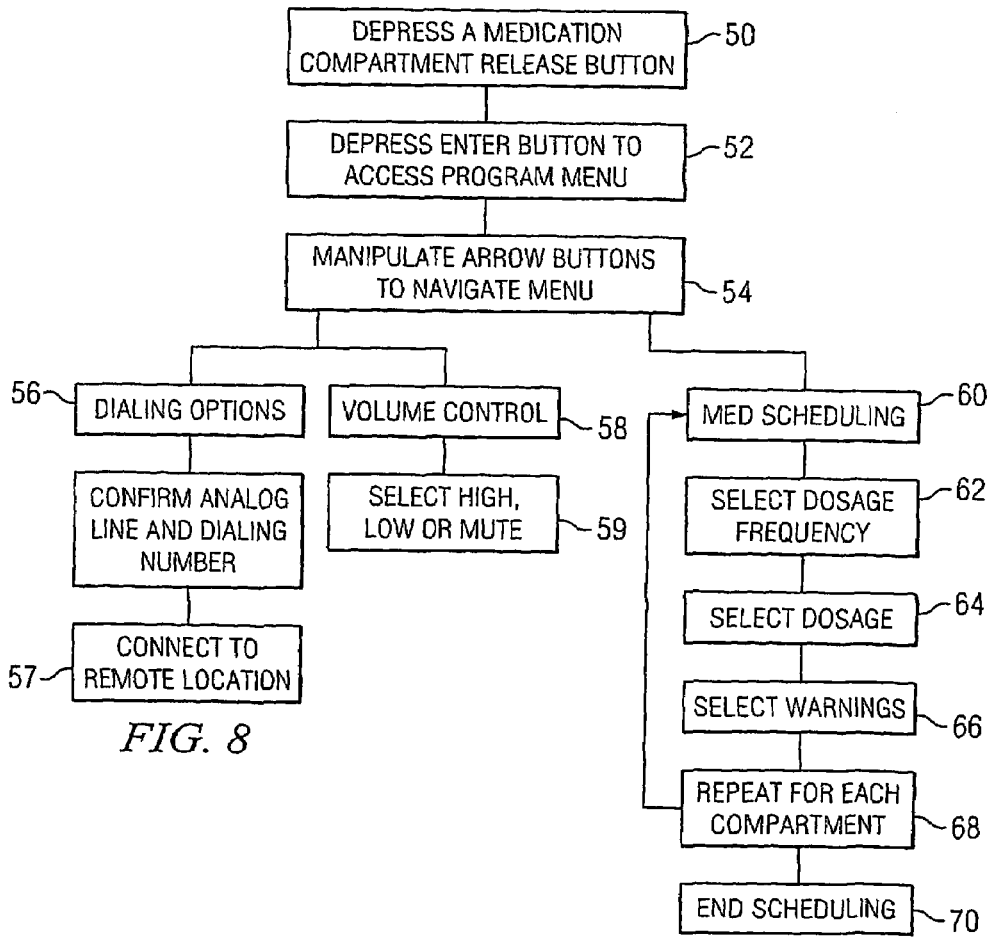
FIG. 8 depicts a flow chart displaying some of the programmable features of an embodiment of the present invention.

FIG. 8 shows a typical programming structure that may be used with the medication compliance device. Each medication compartment of the embodiments shown in FIG. 1 and FIG. 2 are typically programmed separately, although alternative embodiments may include programming two or more compartments 22 at the same time. In another embodiment, the programming instructions may be downloaded from a remote device so that all of the compartments may be programmed at substantially the same time.

Still referring to FIG. 8, a "manual" programming procedure generally begins by pressing the medication compartment button 50 disposed proximate the medication compartment to be programmed. A predetermined signal to the user, such as for example, the opening of a selected compartment lid opens, an "Enter" button 52 (or any other suitably functional button) is depressed to access the programming menu. The programming menu for the embodiment shown in FIGS. 1 and 2 include four options: (1) Dialing Options 56, (2) Volume Control 58, and (3) Med Scheduling 60, (4) Choice of language. The user may depress arrow keys 54 to select one of the menu options. In the embodiment shown in FIG. 2, the arrow keys include up and down buttons 18A. In another embodiment as shown in FIG. 1, in addition to the up and down arrow keys, a user may use left and right arrow keys 18 to select options displayed on the same line of LCD display. The following discussion will describe the various menus and submenus with the understanding that the menu options are selected and the navigation is controlled using the up and down arrow keys 54, and the "Enter" button 52.

The Dialing Options 56 menu selection will be discussed in detail below in the description of the remote communication abilities of the medication compliance device 10. In essence, the Dialing Options 56 includes selecting a type of remote connection, for instance, via analog or digital line; selecting a dialing number in case of analog line, and a command for carrying out remote connections. The Volume Control 58 option enables the user to select a volume level 59 for audible alerts generated by the medication compliance device. The volume levels 59 may include, for example, "high," "low," and "mute" settings, among other volume level settings. Other embodiments may also include, for example, graduated volume level settings. At the end of submenu of Dialing Options 56 and Volume Control 58, the user can come back to the main menu.

The Med Scheduling menu 60 includes several submenus. The first submenu displayed on the LCD is the Dosage Frequency submenu 62. The user can select a dosage that may be, for example, "Once a Day," "Twice a Day," "Three Times a Day," or "Four Times a Day." Other dosage frequencies may also be used in various embodiments of the invention.

After selecting a Dosage Frequency 62 for a selected compartment, the Dosage 64 submenu is displayed on the LCD and the LED attendant to the compartment is illuminated. The user may then select a number of pills to be taken per dose from the selected compartment. For example, the user may select between dosage options such as "Take One," "Take Two," "Take Three," or "Take Four." As described with respect to the dosage frequency, other embodiments may include additional dosage selections in addition to those described herein.

After selecting the Dosage 64, the Warnings 66 submenu is displayed on the LCD. The user or caretaker may select from several warnings associated with the medication disposed in the selected compartment. For example, the treating physician may indicate that the medication should be taken with food. The appropriate "Take With Food" warning may be selected by the user so that it will be displayed in the LCD when the next lid opening occurs. For example, the following warnings, in addition to other warnings, may be selected by the user:

Take With Food
Take With Meals
Take With Water
Avoid Alcohol
May Cause Drowsiness Moreover, the user may select multiple warnings for a single medication and/or compartment.

The user may elect to End Scheduling 70 after completing the programming steps. Alternatively, the user may then repeat 68 the aforementioned steps for each compartment for review and edit purposes, and the newly made selections override previous input.

To start programming for another compartment, a user depresses the button 24 of a desired medication compartment 22, and follows steps outlined in FIG. 8. In another embodiment, several compartments could be programmed at the same time, if the compartments are individually identified, for instance, as compartment A, B, C or D. At the step of Med Scheduling 60, a user can first select a so named compartment 22, then proceed to program this and other compartments without leaving the submenu of Med Scheduling 60. In yet another embodiment, a user can manually input information not previously stored by selecting letters and numbers from a panel of alphabetical letters and numbers.

The medication compliance device uses the settings selected by the user to compute the relative dosage intervals. For example, when the lid of the programmed compartment is closed, the displayed time of the "Last Dose" is set to 0 hours and 0 minutes and the displayed time to the "Next Dose" is set according to the Dosage Frequency 62 selected by the user. For example, if the user selected the "Twice a Day" dosage frequency, the time to the "Next Dose" is displayed on the LCD as 12 hours and 0 minutes. The hours/minutes of interval length is determined by dividing the number of dosings prescribed per day into 24. Note that the time to the "Next Dose" is calculated from the time the lid of the selected compartment is opened rather than from the time at which the previous dosage interval has elapsed. Further, the sum of the times displayed for the "Last Dose" and "Next Dose" should equal the interval length for the selected compartment.

Note that the various medication compartments may also be reprogrammed using the same or a similar procedure when, for example, different medications, dosages, and the like are prescribed by a physician. Reprogramming may be accomplished using the steps described above or a similar process, or new programming instructions may be downloaded. Alternatively, the device may include information (stored in memory) related to a plurality of medications so that the preprogrammed information (e.g. preprogrammed information related to specific medications) may be accessed by the user and used to program the device. This option may enable faster programming and may enable a physician to preprogram the device for medications likely to be prescribed to a specific patient. The procedure set forth above may also be used to program device 4 set forth in FIG. 2, with features 16A, 18A, 20A, 22A and 23 corresponding to 16, 19, 20 22 and 23 of the device shown in FIG. 1.

Signaling and Recording Functions

Figure 9:
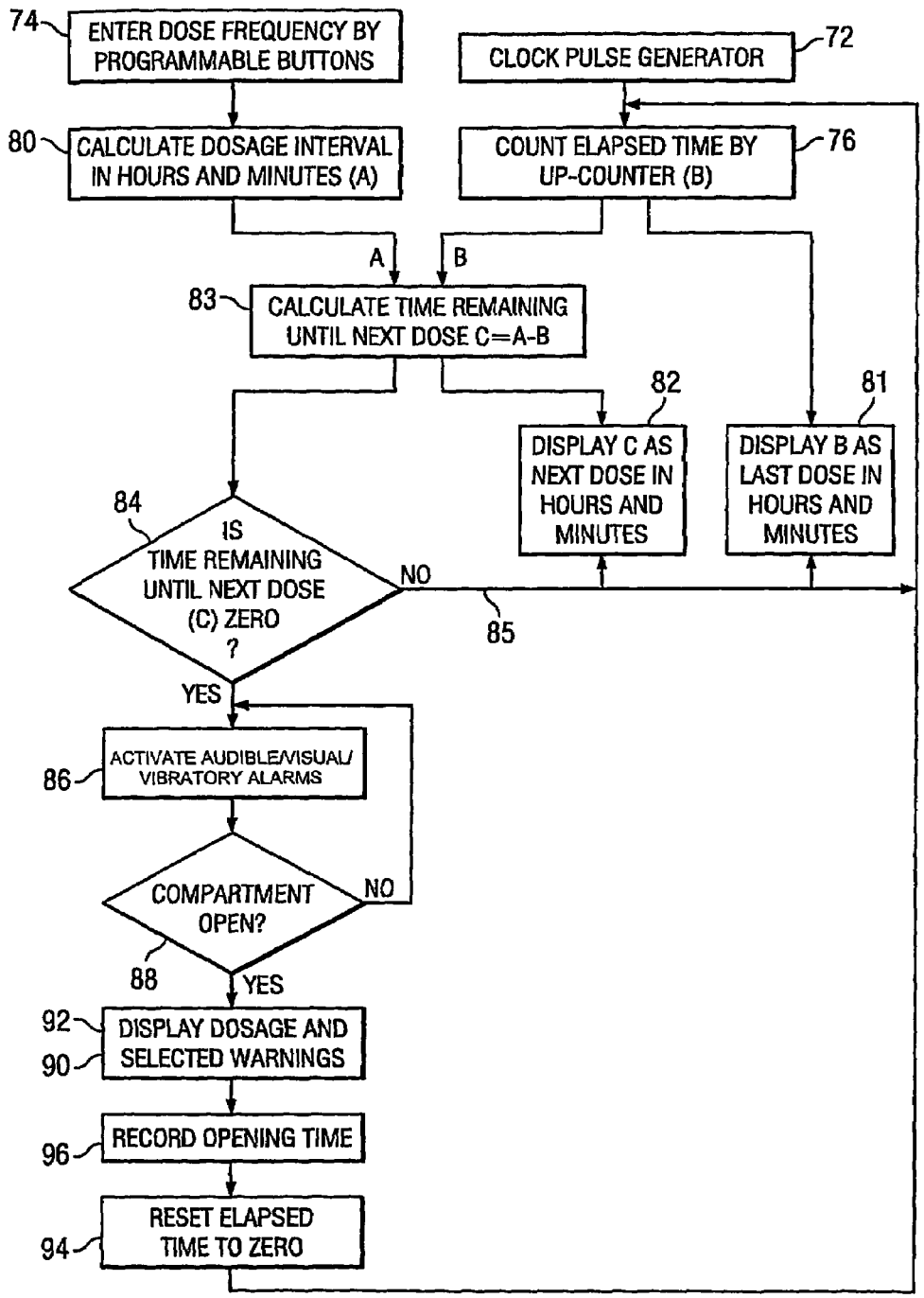
FIG. 9 depicts a flow chart displaying a signaling and alert decision tree according to an embodiment of the present invention.

After the medication compliance device has been programmed, the device will alert the user when the next dose is due to be taken. FIG. 9 shows a flow chart illustrating the Signaling and Recording Functions.

A real time clock, is included in the body and operatively linked to the microprocessor to time internal operations in the compliance device. In one embodiment, a 32 KHz crystal oscillator controls all timing of the device, and in another embodiment, a setting for the clock is 4 Hz. When a user enters the dosage frequency for a particular type of medication via the programming button 74, the microprocessor calculates the Dosage Interval 80 based on the dosage frequency programmed.

Still referring to FIG. 9, when a desired Dosage Interval is established, an up-counter within the electronic device begins to count elapsed time 76 utilizing the internal clock. The up-counter provides two outputs, one representing elapsed time (B) and shown on the display as Last Dose presented in hours and minutes 81. The other output representing time remaining until next dose (C) is calculated in subtractor 83 by subtracting the elapsed time (B) from the Dosage Interval (A). The result of this subtractor is shown on display as Next Dose presented in hours and minutes 82. Whenever sufficient time has elapsed, and the outputs from the subtractors 84 are zero, the visual and audible alarms 86 are activated. If the time for next dose is not yet reached, the LCD may continue display "Last Dose" and "Next Dose", and the up-counter may continue counting the elapsed time 85. In another embodiment, the device goes to "sleep mode" to conserve energy, and it can be revived when the time to take next dose approaches or by a user's action of pressing on a lid release button or a program button.

When a user opens one of the medication compartments 88 to retrieve medicine in response to alert, the action triggers a number of events. First, the display displays dosage information 92 and selected warnings 90. Second, the opening of the compartment 88 is treated as a dosing event of compliance, and the time and the supposed dosage of a particular type of medication is recorded in the memory 96. Third, opening compartment 88 resets the Last Dose (elapsed time) to zero hour and zero minute 94, and restarts a new cycle of events. Note that the order of actions triggered by the opening of compartments is not critical.

In another embodiment, when it is within a medically acceptable time frame to take a medication, for instance, within 20% of dosage period, the microprocessor could activate the display, and signal means to alert the user. When a user opens a compartment door in response to these alerts and within the designated dosage period, the action is registered as an event of compliance. This design aims to provide flexibility for a user within medically acceptable terms and by so doing it may potentially increase compliance rate.

When an audible alert is employed 86, it sounds a number of beeps (or similar audible signals) 86 at a volume selected using the Volume Control menu (58 in FIG. 7). In a preferred embodiment of the medication compliance device, the number of beeps corresponds to the number of pills that should be taken from the selected compartment. For example, if the user is supposed to take three pills from the selected compartment (e.g., as the current dose), the audible alert will sound three times in a repeated cycle to correspond to the dosage. The audible alert continues to beep over a gradually lengthening cycle until the selected compartment is opened or until the user silences the audible alert 86 by, for example, lightly pressing the corresponding medication compartment button. The device may be programmed so that the audible alert 86 ceases to sound after a selected period of time (e.g., several hours). The lengthening cycle may be selected so that a first interval between beeps is approximately 10 seconds, a second interval is approximately 20 seconds, a third interval is 60 seconds, and the like. In another embodiment the audible alerts are pre-recorded voice announcements that remind the user how many pills to remove and the box number from which to remove them. When the lid is opened, the voice may repeat the warnings appropriate to the same compartment.

When a visual alert is employed at 86, it operates in a similar manner. For example, the LED associated with the selected medication compartment 88 may blink to provide a visual alert when the dose from the compartment is due to be taken. The visual alert blinks in a manner similar to beeps generated by the audible alert. For example, if the user is supposed to take three pills from the selected compartment, the LED will blink three times in a repeated cycle to correspond to the dosage. As described above, multiple LEDs may be positioned proximate each compartment, and a selected number of the LEDs may illuminate to correspond to the dosage to be taken from the compartment. Note that the visual alert may be programmed so that it continues indefinitely until the medication compartment is opened. Alternatively, the visual alert may be programmed to cease after a selected time period in a manner similar to the audible alert or to operate on a gradually lengthening cycle as described above.

When the user acknowledges the audible and/or visual alerts by, for example, opening the designated medication compartment 88, the audible alert may be cancelled and the visual alert may continue to indicate the number of pills to be taken from the compartment. Alternatively, both the audible and visual alerts may be cancelled by opening the medication compartment.

When the user opens the medication compartment 88 as a result of the audible and/or the visual alerts, the LCD 92 may display the dosage (e.g., the number of pills to be taken from the selected compartment) and any programmed warnings 90 until the lid is closed. If more than one warning has been programmed for the selected compartment, the LCD 92 may display the dosage and then sequentially display the programmed warnings 90. The time and dosage memory, for example, the time at which the lid was opened, the number of pills that should have been taken at that time, and the like, and calculates the next dosage interval in relative time terms. Elapsed time is then set to zero 94. The process then repeats as indicated in FIG. 9.

Note that the process is similar for other compartments and the illustration showing the operation of a single compartment is intended to clarify the operation of the medical device. It is also possible to program more than one compartment to alert at the same time so that more than one type of medication can be taken at a selected time. Example shown in FIG. 9 is exemplary and is not intended to limit the scope of the invention.

Remote Communication

The compliance data recorded by the medication compliance device, including the opening time of the compartment lid, the new dosage interval (e.g., in relative time), and the number of pills taken during the day, during the interval, etc., are stored in the memory that is operatively coupled to the microprocessor. The memory may be accessed in several different manners. First, the memory may be accessed via a remote connection formed by, for example, an analog or digital phone line, an Internet connection, a wireless or infrared connection, or any other suitable connection known in the art so that the data stored in the memory may be uploaded to a server operated by, for example, the treating physician. The remote connection may be made directly with the device (e.g., using a phone line or other connection that connects directly to the medication compliance device via the communication port 30 as shown in FIG. 1. Alternatively remote communication can be established via the communication port 45 disposed in the cradle (FIG. 2) and the signal contacts (44 of the cradle and of the device) between the portable device and the cradle. Accordingly, the communication port (30 in FIG. 1 or 45 in FIG. 2) may be a phone plug, a serial port, a USB connection, or any other suitable communication connection known in the art.

Regardless of the type of remote connection used, the device may be programmed to upload data to a server or another remote device in selected intervals. For example, the device may be programmed to upload data every day, every two days, every week, and the like. One embodiment of the invention is adapted to upload data in the manner shown in FIG. 10. While the embodiment discussed below with respect to FIG. 10 uses an analog telephone line directly connected to the medication compliance device via the communication port to form the remote connection, the embodiment is only intended to illustrate the remote communication capabilities of the invention. Therefore, the invention is not intended to be limited to a device that uses an analog telephone line to establish a remote connection or to a device that includes a communication line that is connected directly to the medication compliance device.

Figure 10:
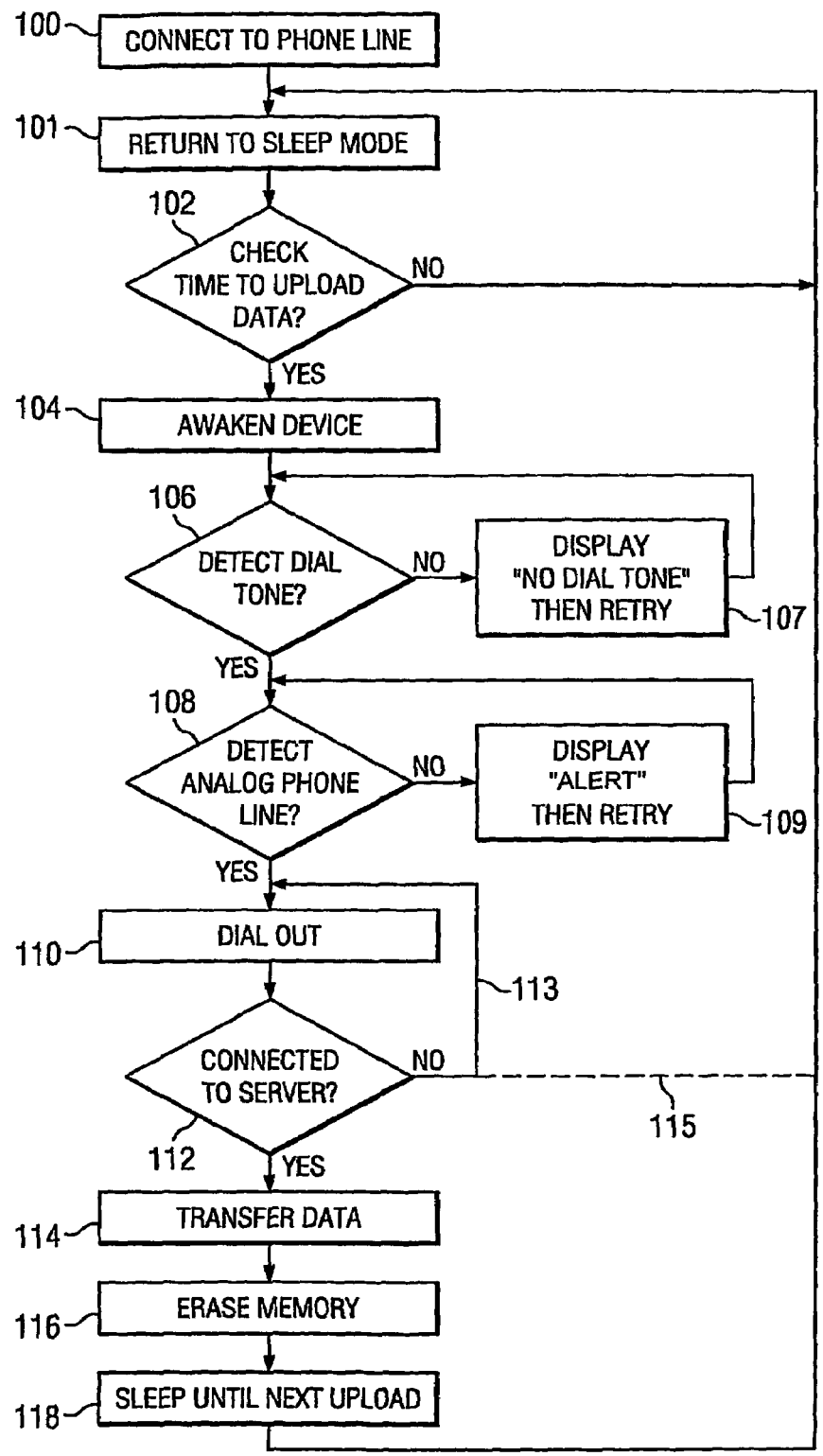
FIG. 10 depicts a flow chart displaying a remote communication decision tree according to an embodiment of the present invention.

Referring to the embodiment discussed in FIG. 10, the medication compliance device is first directly connected to a communications line or wireless signal 100. The device is programmed to sleep 101 for a selected interval and to then upload data periodically according to a selected time interval 102. Therefore, when the internal clock within the medication compliance device determines that it is time to upload data, the device awakens 104 (e.g., powers on into an active mode) and checks to see if a dial tone or other communications signal is available 106. For example, in one embodiment the device checks for a dial tone 106 periodically (e.g., every 10 seconds) after the device is awakened.

If the device does not detect a communications signal, such as a dial tone, the device may display a message on the LCD such as "No Dial Tone" 107 and may wait for a selected time interval (e.g., one minute, 10 seconds, etc.) before checking for a dial tone 106 again. The delay allows time for the user to evaluate the problem and attempt to achieve an effective connection. Thereafter, the device will continue to check for a dial tone after each selected time interval (e.g., every 10 seconds) for a selected time before returning to a "sleep" mode if no dial tone is detected after a selected number of tries.

If a dial tone is detected, the device checks to determine if the phone line connection is an analog connection or a digital connection 108. If the connection is digital, the device displays "Use Analog Line" 109, on the LCD. The device then allows a selected time period before checking the phone connection again. The time period may be, for example, 10 seconds or several minutes, and the time period is not intended to be limiting. In another embodiment, the user could select the type of connection by using programming buttons.

If the remote connection is via an analog phone line, the device attempts to dial out 110 and establish a connection with the remote server. The number dialed by the device is preprogrammed into the memory that is operatively coupled to the microprocessor. The number may be changed by downloading a new number from the remote server or by connecting to a remote computer or other remote device as required. In other embodiments, the user may select from several numbers stored in the memory or may manually enter new numbers using the programming buttons and the like. If the device cannot connect with the remote server, the LCD may display a message such as "Try Again Later" so that the user knows the status of the connection attempt. The device may then either redial immediately 113 or "sleep" 115 for a selected period of time before redialing. For example, the device may sleep for a period of 10 minutes before redialing so that the user has an opportunity to connect the device to a suitable phone line.

If a connection with the server is established 112, the server may attempt to verify a serial number associated with the device and stored in the device memory. If the serial number is valid, the server may proceed with accessing data stored in the device memory. However, if the server does not detect a valid serial number, the server may direct the device to sleep indefinitely and may display "Call Help Desk" and the like on the LCD.

If a connection is established and a valid serial number is detected by the server, the server may direct the device to upload data 114 via the phone connection. As data is being transferred, the message "Transferring" may be displayed by the LCD. If the data transfer is interrupted for any reason or is incomplete, the server will disconnect from the device and a message such as "Try Again Later" will be displayed on the LCD. Thereafter, the medication compliance device may attempt to redial in a manner similar to that described above. Note that the memory will not be erased until a complete transfer of data is achieved.

If the data transfer is complete (note that a complete data transfer may be indicated by the server receipt of an end of file (EOF) character and the like), the server will perform an immediate analysis of the data to check for gaps in the data, suspicious usage patterns, and the like.

The server may then execute algorithms that translate the uploaded data into daily usage patterns. For example, the algorithms may add the newly uploaded data to existing data corresponding to the specific user already stored in the server and transform the relative time format of the newly uploaded data into a 24-hour format so that a physician or analyst can determine the user's medication usage patterns. Note that other types of analyses may be performed on the data and the examples described herein are not intended to be limiting. For example, algorithms may be used to detect if a user is taking medication more often than prescribed (e.g., if the recorded compartment openings are more frequent than prescribed).

If, for example, usage patterns exceed the prescription levels by a selected factor if the data is incomplete, or if the user is behind in a payment schedule, the server may display a message such as "Call Help Desk" on the LCD and direct the device to sleep indefinitely. The user must then contact the help desk in order to "revive" the medication compliance device.

If the connection is made and the data transfer is complete, the server will erase the data from the memory 116 of the medication compliance device so that new events may be recorded prior to the next upload. The server may then display a "Transfer OK" message on the LCD to let the user know that the transfer is complete and has been processed. The server may also alert the user that the users' data and progress may be accessed at a selected website. Moreover, the server may then download additional information to the medication compliance device, including new or updated programming instructions for the compartments, new or updated operating system software for the microprocessor, new dial-up phone numbers, and the like. After these actions are complete, the server may direct the medication compliance device to time out the dial tone sensing function (sleep until next upload) 118, for example, for 24 hours or for another selected period.

Remote Access to User Data

Authorized users may access data stored on the server via, for example, an Internet connection. For example, by logging on to a website hosted by a server or an associated device, the user or a remote caregiver may be able to check their progress with respect to their compliance with a course of treatment prescribed by a physician. In some embodiments, after data has been uploaded, the server may display a message on the LCD directing the user to a specific website.

The user may log on to the specified website using a unique username and password assigned by, for example, the physician. The server may interpret the username and password and allow the user to have limited access to data, status reports, charts, and the like related to the data uploaded by the medication compliance device. In another embodiment, the PIN or "user code" could be used to identify compliance data and the subsequent analysis. The user may also view feedback, instructions, or other information provided by the physician, a technician, or others associated with the treatment program. The following are examples of the types of information that may be displayed on the website and accessed by the user:

performance charts
specific compartment data (e.g., the number of pills taken per compartment per day, week, etc.)
physician feedback
additional instructions from the physician
directions to call the Help Desk or the physician
information related to a next scheduled appointment
overall compliance data
information related to programming changes with respect to the medication compliance device
useful tips and information related to the operation of the medication compliance device
online instruction manuals related to the operation and/or the programming of the medication compliance device
pill reordering information
online sites to obtain detailed medication information Note that the aforementioned list is provided to show specific examples of types of data that may be viewed. The list is not intended to limit the scope of the invention. After the user has completed the visit to the website, they will log off of the website.

EXAMPLE 1

Usage Designed for HIV-positive Patients

The present invention can be used to remind and help compliance of HIV positive patients taking multiple medications. The highly active anti-retroviral therapy (HAART) is the current mainstay of treating HIV infection, universally reducing viral load and increasing immune function (Autran et al. 1997, Positive effects of combined antiretroviral therapy on CD4+ T cell homeostasis and function in advanced HIV disease. Science, 277(5322), 112–116). Patients on HAART typically take three antiviral medications as well as various antibiotics against opportunistic infections. Each medication is often taken two, three or even four times a day, resulting in over 12 dosages a day. The medical device in the present invention is particularly suited for helping HIV patients to adhere to this complex and long term medication regimen. Additionally, substantial cognitive impairment occurs over time among HIV patients, which further exacerbates remembering to take pills on an orderly schedule. Further complicating factors are vision impairment which may occur frequently with the AIDS virus. The device function of beeping the appropriate count of pills to be taken provides easy reminder to patients unable to see the LCD or illuminated LED. Other embodiments envision taped voice message announcements at time of lid openings verbally repeating the warnings appropriate to the compartment and the number of pills removed.

There are several classes of anti-HIV drugs including 1) Nucleoside/Nucleotide Reverse Transcriptase Inhibitors (NRTIs); 2) Non-Nucleoside Reverse Transcriptase Inhibitors (NNRTIs);Protease Inhibitors (PIs); and other classes of drugs such as Entry inhibitors. Both NRTIS and NNRTIS target the reverse transcriptase to block the viral replication in a person's blood. The PIs inhibit the protease which is required for protein processing to package viral particles.

An initial HAART regimen often includes two to three drugs in the NRTI, and one drug in the NNRTI class. Due to the high mutation rate of HIV virus resulting high frequency of drug resistance, and also due to the potential severe side effects associated taking anti-HIV drugs, the initial HAART regimen has a high fail rate, and often needs to be altered later on. The PIs is sometimes reserved for later regimens for patients failed NRTIs and NNRTIs. Similarly, other classes of anti-retroviral drugs such as the Entry Inhibitors also provide another line of defense for the HIV-patients.

Most of the HIV-positive patients may eventually develop AIDS, the acquired immune deficiency syndrome. The weakened immune system makes the patient susceptible to cancers and various opportunistic infections (OIs) including from bacteria, fungi, protozoa, and viruses. When a patient dies of AIDS, opportunistic infections often are the at cause of death.

Based on the clinical data available, the United States Department of Health and Human Services (DHHS) make recommendations based on the value of different anti-HIV drugs. For the initial HAART regimen, DHHS recommends combining the "preferred" NRTIs such as Retrovir (AZT) with Epivir (3TC), Zerit (d4T) or Viread (tenofovir), plus either the NNRTIs such as Sustiva (efavirenz) or the PIs such as Kaletra (lopinavir/ritonavir). Table 1 lists selected anti-AIDS drugs and information regarding their classes, dosage, frequency, warning, and side effects. The selected drugs listed in Table 1 only serves as examples and do not meant to be limiting. Similarly, the drug regimens described below only serve to demonstrate the use of device and do not meant to be limiting.

In one preferred embodiment, the HAART includes two NRTI drugs, Zidovudine (AZT) and lamivudine (3TC), and one NNRTI drug efavirenz. In a preferred embodiment, a patient takes Combivir, the pill combining AZT and 3TC, instead of taking both drugs individually.

TABLE 1

Selected Anti-HIV drugs.

| Brand Name | Generic Name/maker | Class | Tablet Content | Adult dosing | Warning | Side Effects |
|---|---|---|---|---|---|---|
| Retrovir ® | zidovudine (AZT), by GlaxoSmithKline | NRTIs | 300 mg | one 300 mg pill, twice a day | Take with food may minimize stomach discomfort | Nausea; stomach discomfort; headache; insomnia. More rarely: Muscle wasting; anemia; neutropenia. May have long-term side effects. |
| Epivir ® | lamivudine (3TC), by GlaxoSmithKline | NRTIs | 150 mg or 300 mg | one 300 mg pill, once a day; or one 150 mg pill, twice a day | Take with or without food | Nausea. May have long term side effect. |
| Combivir ® | AZT + 3TC, by GlaxoSmithKline | NRTIs | 300 mg AZT, 150 mg 3TC | one pill, twice a day | Take with or without food. Food may reduce discomfort. | Nausea; stomach discomfort; headache; loss of appetite. More rarely: Muscle wasting; anemia; neutropenia. May have long-term side effects. |
| Ziagen ® | abacavir (ABC), by GlaxoSmithKline | NRTIs | 300 mg | one 300 mg pill, twice a day | Take with or without food. | Nausea; vomiting, diarrhea, loss of appetite, insomniac |
| Trizivir ® | ABC + AZT + 3 TC, by GlaxoSmithKline | NRTIs | 300 mg AZT, 150 mg 3TC, 300 mg ABC | one pill, twice a day | Take with or without food. Don't take if weigh less than 90 lbs. | Similar side effects as Retrovir, Epivir, and Ziagen. Also may cause hypersensitivity |
| Sustiva ® | efaviren (EFV), by Bristol-Myers Squibbz | NNRTI | 600 mg | one pill, once a day | May cause dizziness. Take on empty stomach and at bed time. | Rash; drowsiness; insomnia; confusion; can't concentrate, dreams; nausea; stomach discomfort; fever; insomnia; elevated liver enzymes. |
| Viracept ® | nelfinavir (NFV) from Agouron Pharmaceutics | PI | 250 mg or 625 mg | preferred method: 2 625 mg pills, twice a day | Take with meal or light snack | Diarrhea; nausea; stomach discomfort; gas; rash; increased liver enzyme levels. May cause long-term side effects. |

In another embodiment, in addition to the three drugs described above, the HAART further includes the PIs nelfinavir. The following teaches how to use the medical device for this 4-drug regimen. The storage position of a particular drug in compartment is only used as example here. When programming for a certain compartment, press the compartment button and push one of the programming button at the same time to bring up the programming menu. Alternatively, press and hold the programming button for a short period, such as two or three seconds, to activate the programming mode.

Programming for Combivir (300 mgAZT and 150 mg 3TC) in Compartment #1:
At the prompt "Dosage": enter "2 pills a day"
At the prompt "Dose Frequency": enter "1 pill twice a day"
At the prompt "Warning": enter "Take with or without food"

Programming for Sustiva (600 mg) in Compartment #2
At the prompt "Dosage": enter "1 pill a day"
At the prompt "Dose Frequency": enter "once a day"
At the prompt "Warning": enter "Take without food"; "Cause nausea" and "Take at bedtime"

When programming for Viracept (625 mg tablet) in Compartment #3
At the prompt "Dosage": enter "4 pills a day"
At the prompt "Dose Frequency": enter "2 pills twice a day"
At the prompt "Warning": enter "Take with food"; "May cause nausea"

In the morning for instance at 7 am, after a patient finished breakfast, the patient could hear one beep and see one flash of the LED followed by a repeat of this pattern for Compartment #1. The patient will take one pill of Combivir. (S)he sees two flashing lights and hears two beeps in rapid succession for Compartment 3 and knows to open Compartment #3 lid and take two pills of Viracept. Opening the compartment terminates the audible and visual alerts. In addition, it is treated as a compliance event and resets the scheduling. The device Compartments #1 and #3 automatically starts to alert the user at 7 pm, 12 hours after the initial dosing. In response to the alerts, the user retrieves one pill of Combivir from Compartment #1 and two pills of Viracept from Compartment #3. Again at bedtime for instance 10 pm, the LED light on the Compartment #2 will flash once and the audible alert will signal one tone to remind the user that it is time to take 1 pill of Sustiva. Opening the compartment #2 is treated as the dosing event and resets the scheduling. In fact, experimental use of the device has shown to greatly improve the pill-taking compliance of the participating HIV-positive patients in (1) correct timing of intervals between pills, (2) correct number of pills to be taken of a certain type, and (3) observance of warnings attendant to pills.

EXAMPLE 2

Multi-medications Against Tuberculosis

In HIV-positive patients, the weakened immune system makes the patient susceptible to various opportunistic infections, and sometimes the patient can develop tuberculosis which is caused by infection with strains of *Mycobacterium tuberculosis*. A combination of four antibiotics are typically prescribed to maintain control over the infection, and the present medical compliance device is ideal for this purpose.

For the first two months of therapy, a combination of four drugs are usually prescribed, and a brief description for each drug is as follows.

Isoniazid (Nydrazid®): One of the most effective antibiotics used to control TB. It is usually taken with a second drug, pyridoxine (Vitamin B6), to help prevent peripheral neuropathy.

Rifampin (Rifadin®): Another powerful antibiotic needed to manage TB. It can cause various side effects such as nausea, vomiting, diarrhea, rash, liver problems, red-orange discoloration of body fluids (e.g., urine), along with a decrease in white blood cells and platelets. Rifampin interacts with some PIs and NNRTIs of anti-HIV drugs, and thus not recommended for HIV-positive patients taking these medicines.

Pyrazinamide: The dose of this drug depends on the body weight of the person being treated. Its side effects are similar to those of rifampin.

Ethambutol (Myambutol®) or streptomycin: The dose of these two drugs depends on the body weight of the person being treated. Ethambutol can cause vision problems and can cause hearing problems.

The most common method used to treat TB, especially for HIV-positive people, is an initial eight weeks-long therapy using all four drugs ever day, followed by continued therapy for four additional months taking isoniazid and rifabutin either every day or two to three times a week. For an HIV-patient with low T cell counts, it is recommended to take rifabutin every day or three times a week (but not two times a week) with regular monitor at clinics.

An alternative course of therapy includes initial two weeks of treatment with the four drugs every day, followed by taking all four drugs two times a week for an additional eight weeks. Subsequently, isoniazid and rifabutin are continued for an additional 16 weeks either two or three times a week. Another course of therapy includes taking the four drugs for six months three times a week. These therapies should be monitored at clinics or by a health professional.

Each of the four drugs is stored in a different medicine compartment, and the device is programmed for each compartment by entering dosage, dose frequency and warning. Programming for weekly regimens can be performed on a computer and communicated to the device through its communication means. The device not only holds multiple drugs to allow easy access, but also reminds a patient to take various drugs at the appropriate time. The compliance data may be transmitted to the physician or professionals who are monitoring the patient's regimen for analysis and feedback.

EXAMPLE 3

Use the Device to Help Control Cardiovascular Conditions

This device could also be used by users who are taking multi-medications for a particular disease, a condition, or for health maintenance, or a combination of these reasons. For instance, it could be useful for a user with a heart condition taking cardiovascular pills, cholesterol-lowering pills, multi-vitamins and other supplements.

While the invention has been disclosed with reference to specific examples of embodiments, numerous variations and modifications are possible. Therefore, it is intended that the invention not be limited by the description in the specification, but rather by the claims that follow:

What is claimed:

1. A portable medication compliance device, comprising:
    a body adapted to be transported by a user;
    a plurality of compartments formed in said body adapted to receive a type of medication, and each of said compartments having a lid operatively coupled thereto;
    a memory disposed in said body;
    at least one display means disposed on said body;
    a microprocessor disposed in said body and operatively coupled to said memory, each of said compartments and said display, said microprocessor programmable to determine time for dispensing medication from each of said compartments, to notify the user when a dose of medication is to be taken from each of said compartments, and to record the opening of each of said compartments in said memory;
    one or more programming buttons disposed proximate said body and operatively coupled to the microprocessor, said programming buttons adapted to enable the user to program said microprocessor;
    wherein said microprocessor is programmable to determine the relative time interval to take a type of medication; and wherein said relative time interval for a type of medication is calculated based on the dose frequency selected by a user via said programming buttons; and wherein opening of medication compartment resets the relative time interval.

2. The device of claim 1, further comprising output means for a signaling device to alert a user of the time to take a type of medication, said output means operatively coupled to and activated by said microprocessor when said relative time interval to take a particular medication expires.

3. The device of claim 1, further comprising a communication port operative to enable the uploading of compliance medication data from said memory to a remote device, said communication port disposed proximate said body and operatively coupled to said microprocessor.

4. The device of claim 1, further comprising a communication port to enable downloading information from the remote device to the microprocessor and memory coupled thereto, said communications port disposed proximate said body and operatively coupled to said microprocessor.

5. The device of claim 2, further comprising a communication port operative to enable the uploading of compliance medication data from said memory to a remote device, said communication port disposed proximate said body and operatively coupled to said microprocessor.

6. The device of claim 2, further comprising a communication port to enable downloading information from the remote device to the microprocessor and memory coupled thereto, said communication port disposed proximate said body and operatively coupled to said microprocessor.

7. The device of claims 1 or 2, wherein said display means is an LCD display and further comprising a plurality of LCD displays for displaying information for individual medication compartment, each of said LCD display disposed proximate each of said medication compartments.

8. The device of claim 3 or 4 wherein said display means is an LCD display and further comprising a plurality of LCD displays for displaying information for individual medication compartment, each of said LCD display disposed proximate each of said medication compartments.

9. The device of claim 5 or 6, where in said display means is an LCD display and further comprising a plurality of LCD displays for displaying information for individual medication compartment, each of said LCD display disposed proximate each of said medication compartments.

10. The device of claims 1 or 2, further comprising a compartment button disposed adjacent one or more of said medication compartments, said compartment buttons operatively responsive to differential mode of activation by a user.

11. The device of claim 10, wherein said differential modes are activated by the user by the number of times the button is pressed by the user, the amount of time the button is depressed, or the time period in which multiple pressings is accomplished.

12. The device of claim 3, further comprising a compartment button disposed adjacent one of said medication compartments, said compartment buttons operatively responsive to differential modes of activation by a user.

13. The device of claim 12, wherein said differential modes are activated by the user by the number of times the button is pressed by the user, the amount of time the button is depressed, or the time period in which multiple pressings is accomplished.

14. The device of claim 4, further comprising a compartment button disposed adjacent one of said medication compartments, said compartment buttons operatively responsive to differential modes of activation by a user.

15. The device of claim 14, wherein said differential modes are activated by the user by the number of times the button is pressed by the user, the amount of time the button is depressed, or the time period in which multiple pressings is accomplished.

16. The device of claim 5, wherein each of said compartment buttons is disposed adjacent one of said medication compartments, said compartment buttons operatively responsive to differential modes of activation by a user.

17. The device of claim 16, wherein said differential modes are activated by the user by the number of times the button is pressed by the user, the amount of time the button is depressed, or the time period in which multiple pressings is accomplished.

18. The device of claim 6, further comprising a component button disposed adjacent tone of said medication compartments, said compartment buttons operatively responsive to differential mode of activation by a user.

19. The device of claim 18, wherein said differential modes are activated by the user by the number of times the button is pressed by the user, the amount of time the button is depressed, or the time period in which multiple pressings is accomplished.

20. The device of claim 7, further comprising a compartment button disposed adjacent one of said medication compartments, said compartment buttons operatively responsive to differential modes of activation by a user.

21. The device of claim 20, wherein said differential modes are activated by the user by the number of times the button is pressed by the user, the amount of time the button is depressed, or the time period in which multiple pressings is accomplished.

* * * * *

UNITED STATES PATENT AND TRADEMARK OFFICE
CERTIFICATE OF CORRECTION

PATENT NO. : 7,158,011 B2
APPLICATION NO. : 10/545382
DATED : January 2, 2007
INVENTOR(S) : Vesta L. Brue Page 1 of 1

It is certified that error appears in the above-identified patent and that said Letters Patent is hereby corrected as shown below:

Col. 2, line 67, replace "2,344194" with -- 2,344,194 --
Col. 5, line 59, replace "including a" with -- including: a --
Col. 10, line 21, replace "1 or" with -- 1) or --
Col. 12, line 16, replace "FIGS. 1 and" with -- FIG. 1 and --
Col. 13, line 2, replace "58, and (3)" with -- 58, (3) --
Col. 14, line 50, replace "19, 20 22" with -- 19, 20, 22 --
Col. 20, line 17, replace "NRTIS and NNRTIS" with -- NRTIs and NNRTIs --
Col. 20, line 36, replace "the at cause" with -- the cause --
Col. 20, line 48, replace "and do not" with -- and are not --
Col. 20, line 50, replace "and do not" with -- and are not --
Table 1, Col. Side Effects, opposite Ziagen, replace "Nausea; vomiting, diarrhea, loss of appetite, insomniac" with -- Nausea; vomiting; diarrhea; loss of appetite; insomniac --
Col. 21, line 53, replace "programming button at" with -- programming buttons at --
Col. 21, line 58, replace "mgAZT" with -- mg AZT --
Col. 23, line 48, replace "ever day" with -- every day --
Col. 25, line 18, replace "where in" with -- wherein --

Signed and Sealed this

Seventeenth Day of April, 2007

JON W. DUDAS
*Director of the United States Patent and Trademark Office*